United States Patent

Yago et al.

[11] Patent Number: 5,879,923
[45] Date of Patent: Mar. 9, 1999

[54] STABLE PLASMIN SOLUTION

[75] Inventors: Hirokazu Yago; Mari Emmi, both of Ryugasaki, Japan

[73] Assignee: Daiichi Pure Chemicals Co., Ltd., Tokyo, Japan

[21] Appl. No.: 973,745

[22] PCT Filed: Jun. 24, 1996

[86] PCT No.: PCT/JP96/01738
§ 371 Date: Dec. 22, 1997
§ 102(e) Date: Dec. 22, 1997

[87] PCT Pub. No.: WO97/01631
PCT Pub. Date: Jan. 16, 1997

[30] Foreign Application Priority Data

Jun. 26, 1995 [JP] Japan ................................. 7-159330
Jun. 26, 1995 [JP] Japan ................................. 7-159331

[51] Int. Cl.⁶ .............................. C12N 9/68; A61K 38/04
[52] U.S. Cl. ....................... 435/217; 435/188; 435/212; 530/300; 530/331; 530/332; 514/2
[58] Field of Search .................................. 435/217, 188, 435/212; 530/300, 331, 332; 514/2

[56] References Cited

U.S. PATENT DOCUMENTS 4,361,652  11/1982  Uemura et al. ........................ 435/188
4,361,653  11/1982  Watanabe et al. ..................... 435/188
4,442,213  4/1984  Heber et al. .......................... 455/217

*Primary Examiner*—Cecilia J. Tsang
*Assistant Examiner*—Abdel A. Mohamed
*Attorney, Agent, or Firm*—Oblon, Spivak, McClelland, Maier & Neustadt, P.C.

[57] ABSTRACT

A plasmin solution, comprising:

(A) plasmin, and (B) the following component (B-1), (B-2) or (B-3):

(B-1) an oligopeptide comprising at least two amino acids bonded to each other, where the two amino acids are selected from the group consisting of lysine, arginine, glycine, alanine, aspartic acid and methionine;

(B-2) at least two amino acids selected from the group consisting of lysine, arginine, glycine, alanine, aspartic acid and methionine; or (B-3) an amino acid selected from the group consisting of lysine, arginine, glycine, alanine, aspartic acid and methionine, and a polyhydric alcohol. This solution is stable, maintains plasmin activity even after long-term storage, and can be used as a reagent for quantitatively measuring α2PI.

20 Claims, 1 Drawing Sheet

STABLE PLASMIN SOLUTION

TECHNICAL FIELD

The present invention relates to a stable plasmin solution useful as a reagent for the quantitative measurement of a blood coagulation and fibrinolysis factor.

BACKGROUND ART

The reaction of an enzyme in the living body is controlled and regulated by its activating substance or a substance inhibiting its reaction, whereby its function is adjusted. For example, in the blood coagulation mechanism, there exists an enzyme inhibitor which inhibits the blood coagulation reaction at the sites other than a vascular injury site or inhibits hypercoagulability and hyperfibrinolysis and by the inhibitor, blood coagulation and fibrinolysis is being controlled and regulated. In the hematological test to investigate the advance of thrombus formation, the quantitative measurement of an enzyme inhibitor has an important meaning. Since the amount of the enzyme inhibitor serves as a suitable index showing the condition of coagulation and fibrinolysis, quantitative measurement of an enzyme inhibitor such as antithrombin III (ATIII) or α2-plasmin inhibitor (α2PI) is carried out.

It has been made cleared that among such enzyme inhibitors, α2PI is one of the most important fibrinolysis inhibiting factors which can control fibrinolysis in the blood and it has attracted attentions as an index for finding hyperfibrinolysis in the living body. The blood level of α2PI is different according to the kinds or symptoms of the diseases. For example, it shows a marked reduction in the case of disseminated intravascular coagulation (DIC) or liver troubles. The blood level of α2PI has therefore been used as an index for screening of such a disease, analysis of the morbid state or judgment of prognosis and also an index for judging drug efficacy at the fibrinolytic treatment.

The quantitative measurement of such an enzyme inhibitor has conventionally been carried out by reacting the enzyme inhibitor with an excess amount of an enzyme and then measuring the residual amount of the enzyme. For example, based on the fact that α2PI inhibits the enzyme plasmin, the amount of α2PI in a biosample (specimen) is measured by reacting α2PI in the specimen with a certain amount of plasmin and then measuring the remaining plasmin activity. In this case, the activity of the plasmin is determined, for example, by measuring the hydrolysis rate of a chromogenic synthetic substrate from a change in the absorbance.

Many of such enzyme inhibitors are serine protease inhibitors and an enzyme for measuring such enzyme inhibitors is serine protease. Proteases such as serine protease each has a site which will become its own substrate within its molecule so that prompt decomposition in the solution and lowering in the protease activity or binding activity with a protease inhibitor are sometimes observed. For example, a human-derived plasmin used for the quantitative measurement of α2PI loses 72% of its protease activity when allowed to stand at 37° C. for one hour and decomposition occurs both in the H chain and L chain (K. N. N. Reddy, Biochem. Biophys, Res. Commun., 92, 1016–1022(1980)).

It is known, on the other hand, that the protease activity of plasmin exhibits improved stability under the presence of fibrinogen, ε-aminocaproic acid and glycerol or at high ion strength (J. Jespersen, Thromb. Res., 37, 3955–404(1986) or under the presence of ε-aminocaproic acid and lysine (K. N. N. Reddy, Progress in Fibrinolysis, 374–379(1981)).

The above methods are however accompanied with the drawbacks that they bring about stabilization only for extremely short time and if plasmin is allowed to stand at 37° C. for one hour, its activity lowers considerably; and that even if 50% glycerol permitting the relative retention of the stability of protease activity is added, the binding activity with a protease inhibitor lowers (M. Shimokawa, Analytical Science, 10, 533–536 (1994)).

The reagent for the quantitative measurement of such an enzyme inhibitor is prepared as a lyophilized product because plasmin cannot be stored in the form of a solution. It must be prepared as a solution right before the measurement. Thus, the conventional reagent involves problems in economy, operability and prompt measurement.

In addition, it is difficult to employ an automatic analyzer for the measurement adopting the conventionally used plasmin solution as a measuring reagent of α2PI, because the solution is highly viscous and besides, in the form of the solution, marked reductions in the activity of plasmin and binding activity of plasmin with α2PI occur.

An object of the present invention is therefore to provide a process for stabilizing plasmin by which the plasmin activity and binding activity of plasmin with α2PI can be maintained stably for a long time even after storage in the form of a solution; and a stable plasmin solution.

DISCLOSURE OF THE INVENTION

Figure 1:
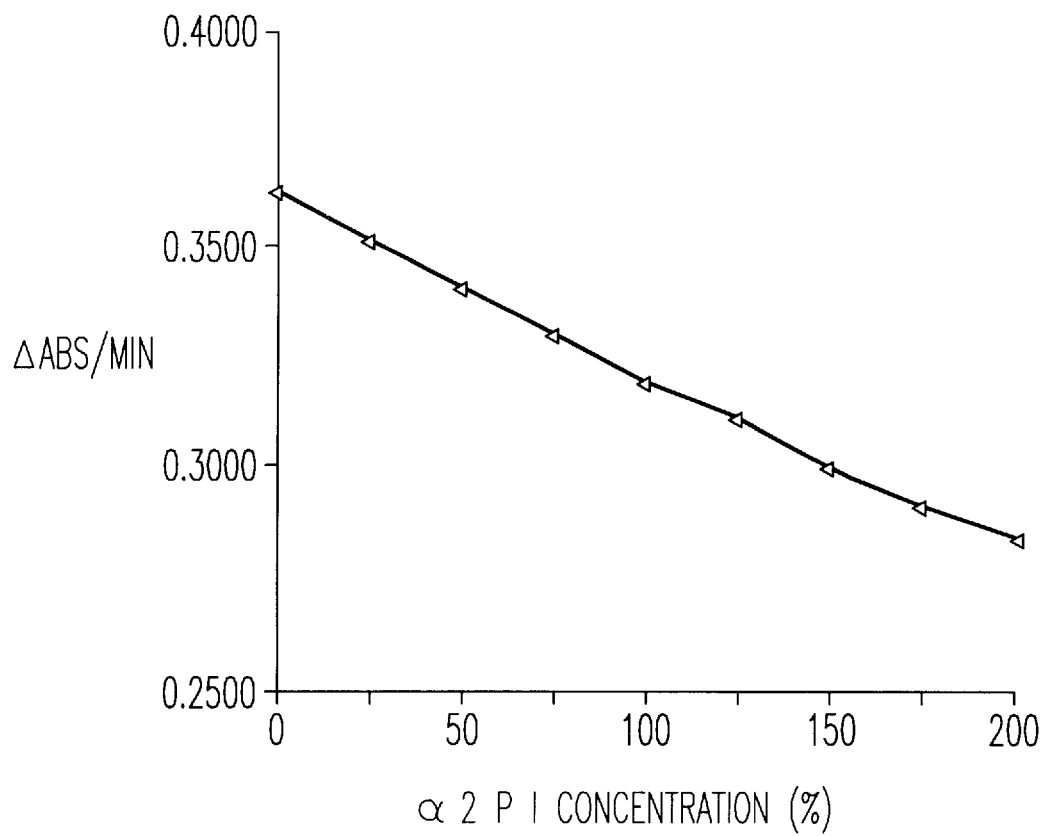
FIG. 1 illustrates a relationship between an α2PI concentration and measured value (ΔAbs/min) when a calibration curve exactness was studied in Example 5.

With the forgoing in view, the present inventors have carried out an extensive investigation. As a result, it has been found that a plasmin solution which is stable in plasmin activity and binding activity with α2PI for a long time and is therefore useful as a reagent for the quantitative measurement of α2PI can be obtained by using specific amino acids or an oligopeptide having said specific amino acids bonded each other, leading to the completion of the present invention.

The present invention therefore provides a plasmin solution comprising:
(A) plasmin and
(B) the following component (B-1), (B-2) or (B-3):
  (B-1) an oligopeptide comprising at least two amino acids bonded each other, said two amino acids being selected from lysine, arginine, glycine, alanine, aspartic acid and methionine;
  (B-2) at least two amino acids selected from lysine, arginine, glycine, alanine, aspartic acid and methionine; or
  (B-3) an amino acid selected from, lysine, arginine, glycine, alanine, aspartic acid and methionine and a polyhydric alcohol.

The present invention also provides a process for the stabilization of plasmin, which comprises adding, to a plasmin solution,
  (B-1) an oligopeptide comprising at least two amino acids bonded each other, said two amino acids being selected from lysine, arginine, glycine, alanine, aspartic acid and methionine;
  (B-2) at least two amino acids selected from lysine, arginine, glycine, alanine, aspartic acid and methionine; or (B-3) an amino acid selected from lysine, arginine, glycine, alanine, aspartic acid and methionine and a polyhydric alcohol.

BEST MODES FOR CARRYING OUT THE INVENTION

As plasmin usable in the present invention, any one of methionyl type (having methionine at its N terminal), glutamyl type (having glutamic acid at its N terminal) and lysyl type (having lysine at its N terminal) can be used. For example, plasmin commercially available from Chromogenics Inc. can be used. These types of plasmin can be used either singly or in combination and it is preferred to use it so that the its activity falls within a range of 0.1 to 10 nkat/ml, particularly 0.3 to 5 nkat/ml. Incidentally, the term "1 nkat" as used herein means an amount of plasmin sufficient for decomposing 1 nmol of a plasmin synthetic substrate (S-2251) per second.

Examples of the oligopeptide usable as the component (B-1) in the present invention include dipeptides and tripeptides obtained by using, in combination, one or more amino acid selected from lysine, arginine, glycine, alanine, aspartic acid and methionine. Among them, dipeptides and tripeptides composed of one amino acid are preferred, with glycyl glycine, glycyl glycyl glycine and alanyl alanine being particularly preferred.

These oligopeptides can be used either singly or in combination. The oligopeptide is preferably added in an amount of 1 to 20 wt. % (which will hereinafter indicated by "%", simply), particularly 5 to 20% based on the whole composition. Based on plasmin in the solution, it is preferably added in an amount ranging from 1 to 2000 mg/nkat, with a range of 10 to 700 mg/nkat being particularly preferred.

When at least two amino acids are used in combination as the component (B-2) in the present invention, they are selected from lysine, arginine, glycine, alanine, aspartic acid and methionine. Among them, the combination of lysine and glycine and that of lysine and alanine are preferred.

It is preferred that these amino acids are added in a total amount of 1 to 20%, particularly 5 to 20% based on the whole composition. It is, on the other hand, preferred to add them in an amount ranging from 1 to 2000 mg/nkat, particularly 10 to 700 mg/nkat, relative to plasmin in the solution.

In the present invention, one of amino acids selected from lysine, arginine, glycine, alanine, aspartic acid andmethionine and a polyhydric alcohol are used as the component (B-3).

As the amino acid usable here, lysine is particularly preferred.

The amino acid is preferably added in an amount of 1 to 20%, particularly 5 to 20% based on the whole composition. Relative to plasmin in the solution, on the other hand, the amino acid is preferably added in an amount ranging from 1 to 2000 mg/nkat, particularly 10 to 700 mg/nkat.

Preferred examples of the polyhydric alcohol usable here include glycerol, ethylene glycol and polyethylene glycol. The polyhydric alcohol is preferably added in an amount of 1 to 50%, particularly 5 to 30%, based on the whole composition.

When an oligopeptide (B-1) or at least two amino acids (B-2) are used as the component (B), a polyhydric alcohol can be added further to obtain a more stable plasmin solution. Examples of the polyhydric alcohol usable here include glycerol, ethylene glycol and polyethylene glycol. In the case where a polyhydric alcohol is added, it is preferably added in an amount of 1 to 50%, particularly 5 to 30% based on the whole composition.

When an oligopeptide (B-1) is used as the component (B), one or more amino acids selected from lysine, arginine, glycine, alanine, aspartic acid and methionine can be used in combination to obtain a more stable plasmin solution. In this case, these amino acids are preferably added in an amount of 1 to 20%, particularly 5 to 20%, based on the whole composition.

When an oligopeptide (B-1) and one or more amino acids are used as the component (B), a polyhydric alcohol can be added further to obtain a more stable plasmin solution. As the polyhydric alcohol usable here, glycerol, ethylene glycol, polyethylene glycol and the like are preferred. When the polyhydric alcohol is added, it is preferably added in an amount of 1 to 50%, with 5 to 30% being particularly preferred.

The plasmin solution according to the present invention is useful as a reagent for the quantitative measurement of α2PI, a standardized solution of plasmin or the like. When the plasmin solution is used as a reagent, quantitative determination of α2PI in a specimen can be effected with high precision by using an ordinarily-employed chromogenic synthetic substrate. No particular limitation is imposed on the chromogenic synthetic substrate. For example, S-2251 (H-D-Val-Leu-Lys-paranitroaniline) or S-2403 (Glu-Phe-Lys-paranitroaniline) produced by Chromogenic Inc. can be suitably used.

EXAMPLES

The present invention will hereinafter be described more specifically by examples. It should however be borne in mind that the present invention is not limited to or by the following examples.

Example 1

To 250 μl of a first reagent having the below-described composition, a normal plasma specimen (containing a predetermined amount of α2PI) and physiological saline were added, each in an amount of 3 μl, respectively, followed by the reaction at 37° C. for 5 minutes. To each of the reaction mixtures, 100 μl of a second reagent having the below-described composition were added. A change in an absorbance at a wavelength of 405 nm per minute was measured. The change in an absorbance at the time when physiological saline was used indicates plasmin activity, that is, a titer to hydrolyze a plasmin synthetic substrate (S-2251) of plasmin. A value obtained by subtracting the remaining activity of plasmin after the reaction of the normal plasma specimen from the plasmin activity of physiological saline indicates the binding activity of plasmin with α2PI.

As a solution to be used for the plasmin solution of a second reagent, used was a 20% glycerol solution containing an additive which will be shown in Table 1. The solution was adjusted to pH 7.4 with sodium hydroxide or hydrochloric acid and then plasmin was dissolved in it. A half portion of the solution was used for measurement on that day, while the remaining half portion was provided for measurement after hermetically sealed and allowed to stand at 37° C. for 4 days. Incidentally, 50% glycerol and 20% glycerol were used for comparison. The results are shown in Table 1.

First reagent:

H-D-Valyl-L-leucyl-L-lysyl-p-nitroaniline ("S-2251"  1.2 mM
produced by Chromogenic Inc.)
25 mM tris buffer (pH 7.4)

Second reagent:

Plasmin  3 nKat/ml
Each plasmin solution (pH 7.4)

*: the term "1 nkat" means an amount of plasmin sufficient for decomposing 1 nmol of S-2251 per second.

TABLE 1

| No. | Additive | Initial value | | Measured after 4 days at 37° C. | | Ratio (%) | |
|---|---|---|---|---|---|---|---|
| | | Activity | Binding activity | Activity | Binding activity | Activity | Binding activity |
| 1 | 50% glycerol | 3517 | 646 | 3520 | 514 | 100 | 80 |
| 2 | 20% glycerol | 2722 | 520 | 293 | 83 | 3 | 3 |
| 3 | 10% lysine | 3017 | 416 | 2960 | 377 | 98 | 91 |
| 4 | 10% arginine | 2916 | 570 | 2678 | 388 | 92 | 68 |
| 5 | 10% alanine | 2969 | 660 | 1974 | 501 | 66 | 76 |
| 6 | 10% glycine | 2853 | 604 | 1945 | 457 | 68 | 76 |
| 7 | 10% glycyl glycine | 2668 | 416 | 2655 | 352 | 100 | 85 |

(1) Additives in Nos. 3 to 7 were dissolved in a 20% glycerol solution.
(2) The initial values and values measured when the plasmin solution was allowed to stand at 37° C. for 4 days are each indicated by the unit of ΔAbs/min.
(3) "Activity" means a titer to hydrolyze a plasmin synthetic substrate (S-2251).
(4) "Binding activity" means the binding ability of plasmin with α2P1 and is a value obtained by subtracting, from the activity value of plasmin, residual plasmin activity at the time when the normal plasma specimen was reacted.
(5) "Ratio" means a ratio of the activity or binding activity measured after the plasmin solution was allowed to stand at 37° C. for 4 days supposing that the activity or binding activity at the initial stage is 100%, respectively.

As is apparent from the results in Table 1, it has been found that the plasmin solution according to the present invention was maintained stably without deteriorations in the plasmin activity and α2PI binding activity and that the viscosity of the plasmin solution was low.

Example 2

As in Example 1, various plasmin solutions having the compositions as shown in Table 2 were prepared and the plasmin activity and binding activity of plasmin with α2PI were measured at the time when the solutions were prepared and after the solutions were stored at 37° C. for 2 days. The results are shown in Table 2.

TABLE 2

| No. | Additive | Initial value | | Measured after 2 days at 37° C. | | Ratio (%) | |
|---|---|---|---|---|---|---|---|
| | | Activity | Binding activity | Activity | Binding activity | Activity | Binding activity |
| 1 | 50% glycerol | 3666 | 674 | 3689 | 593 | 101 | 88 |
| 2 | 10% Lys | 2915 | 430 | 2221 | 345 | 76 | 80 |
| 3 | 10% Lys + 2% Ala | 2894 | 412 | 2456 | 405 | 85 | 98 |
| 4 | 10% Lys + 2% Gly | 2873 | 426 | 2475 | 389 | 86 | 91 |
| 5 | 10% Gly—Gly | 2766 | 469 | 2527 | 419 | 91 | 89 |
| 6 | 10% Gly—Gly + 2% Ala | 2722 | 461 | 2589 | 425 | 95 | 92 |
| 7 | 10% Gly—Gly + 2% Gly | 2705 | 447 | 2572 | 428 | 95 | 96 |

(1) Additives in Nos. 3 to 7 were dissolved in a 20% glycerol solution.
(2) The initial values and values measured after the plasmin solution was allowed to stand at 37° C. for 2 days are each indicated by the unit of ΔAbs/min.
(3) "Activity" means a titer to hydrolyze a plasmin synthetic substrate (S-2251).
(4) "Binding activity" means the binding ability of plasmin with α2P1 and is a value obtained by subtracting, from the activity of plasmin, residual plasmin activity at the time when the normal plasma specimen was reacted.
(5) "Ratio" means a ratio of the activity or binding activity measured after the plasmin solution was allowed to stand at 37° C. for 2 days supposing that the activity or binding activity at the initial stage is 100%, respectively.
(6) Gly—Gly: glycyl glycine, Ala: alanine, Gly: glycine and Lys: lysine.

As is apparent from Table 2, it has been found that the plasmin solution according to the present invention was maintained stably without lowering the plasmin activity and α2PI binding activity.

The plasmin solution No. 3 containing 10% lysine and 2% alanine had a viscosity of 1.40 cp when measured at 25° C. by using VISCOMATE (manufactured by Yamaichi Denki Kogyo), while the plasmin solution No. 3 in Table 2 containing 10% lysine and 20% glycerol had a viscosity of 2.47 cp. On the other hand, the plasmin solution containing 50% glycerol had a viscosity of 6.98 cp. Thus, the plasmin solution according to the present invention has low viscosity so that it can be analyzed by an automatic analyzer.

Example 3

As in Example 1, various solutions having the compositions as shown in Table 3 were prepared and plasmin activity and binding activity of plasmin with α2PI were measured at the time when the solutions were prepared and after they were stored at 37° C. for 25 days. Incidentally, the physiological saline and normal plasma specimen were used each in an amount of 5 µl. The results are shown in Table 3.

As is apparent from the results of Table 3, it has been that the plasmin solution of the present invention was maintained stably without deteriorations in the plasmin activity and α2PI binding activity, and that the plasmin solution had a low viscosity.

Example 4

As in Example 1, plasmin activity and plasmin α2PI binding activity of various plasmin solutions having the compositions as shown in Table 4 were measured at the time when they were prepared and after they were stored at 37° C. for 9 days. Incidentally, the physiological saline and the normal plasma specimen were used each in an amount of 5 µl. The results are shown in Table 4.

TABLE 3

| No. | Additive | Initial value | | Measured after 25 days at 37° C. | | Ratio (%) | |
| --- | --- | --- | --- | --- | --- | --- | --- |
| | | Activity | Binding activity | Activity | Binding activity | Activity | Binding activity |
| 1 | 50% glycerol | 3115 | 976 | 2917 | 704 | 94 | 72 |
| 2 | Gly—Gly, Glycerol, L, A, G | 2233 | 475 | 2240 | 515 | 100 | 108 |
| 3 | Gly—Gly, Glycerol, L, A | 2206 | 463 | 2109 | 478 | 96 | 103 |
| 4 | Gly—Gly, Glycerol, L, G | 2221 | 461 | 2168 | 457 | 98 | 99 |
| 5 | Gly–Gly, Glycerol, A, G | 2297 | 536 | 2228 | 538 | 97 | 101 |
| 6 | Gly—Gly, Glycerol, L | 2166 | 457 | 2050 | 468 | 95 | 102 |
| 7 | Gly—Gly, Glycerol, A | 2261 | 518 | 2185 | 523 | 97 | 101 |
| 8 | Gly—Gly, Glycerol, G | 2236 | 510 | 2150 | 517 | 96 | 101 |
| 9 | Gly—Gly, Glycerol | 2288 | 557 | 2100 | 541 | 92 | 97 |

(1) The initial values and values measured after the plasmin solution was allowed to stand at 37° C. for 25 days are each indicated by the unit of ΔAbs/min.
(2) "Activity" means a titer to hydrolyze a plasmin synthetic substrate (S-2251).
(3) "Binding activity" means the binding ability of plasmin with α2P1 and is a value obtained by subtracting, from the activity of plasmin, residual plasmin activity at the time when the normal plasma specimen was reacted.
(4) "Ratio" means a ratio of the activity or binding activity measured after the plasmin solution was allowed to stand at 37° C. for 25 days supposing that the activity or binding activity at the initial stage is 100%, respectively.
(5) Gly—Gly: 10% glycyl glycine, L: 2% lysine; A: 2% alanine, G: 2% glycine and Glycerol: 10% glycerol.

TABLE 4

| No. | Additive | Initial value | | Measured after 4 days at 37° C. | | Ratio (%) | |
| --- | --- | --- | --- | --- | --- | --- | --- |
| | | Activity | Binding activity | Activity | Binding activity | Activity | Binding activity |
| 1 | 10% Gly—Gly | 2675 | 607 | 2048 | 492 | 77 | 81 |
| 2 | 10% Gly—Gly + 10% Glycerol | 2842 | 572 | 2685 | 580 | 95 | 101 |

TABLE 4-continued

|  |  | Initial value | | Measured after 4 days at 37° C. | | Ratio (%) | |
|---|---|---|---|---|---|---|---|
| No. | Additive | Activity | Binding activity | Activity | Binding activity | Activity | Binding activity |
| 3 | 10% Gly—Gly + 10% EtGlycol | 2921 | 582 | 2645 | 561 | 91 | 96 |

(1) The initial values and values measured after the plasmin solution was allowed to stand at 37° C. for 9 days are each indicated by the unit of ΔAbs/min.
(2) "Activity" means a titer to hydrolyze a plasmin synthetic substrate (S-2251).
(3) "Binding activity" means the binding ability of plasmin with α2PI and is a value obtained by subtracting, from the activity of plasmin, residual plasmin activity at the time when the normal plasma specimen was reacted.
(4) "Ratio" means a ratio of the activity or binding activity measured after the plasmin solution was allowed to stand at 37° C. for 9 days supposing that the activity or binding activity at the initial stage is 100%, respectively.
(5) Gly—Gly: glycyl glycine, Glycerol: 10% glycerol and EtGlycol: ethylene glycol.

As is apparent from the results of Table 4, it has been found that the plasmin solution of the present invention containing glycyl glycine was maintained stably without deteriorations in the plasmin activity and binding activity of α2PI.

The plasmin solution No. 2 containing 10% glycyl glycine and 10% glycerol had a viscosity of 1.89 cp as measured at 25° C. by VISCOMATE (manufactured by Yamaichi Denki Kogyosha). The plasmin solution containing 50% glycerol, on the other hand, had a viscosity of 6.98 cp at 25° C. The plasmin solution according to the present invention has thus a low viscosity and can therefore be provided for use in the measurement using an automatic analyzer.

Example 5

As in Example 1, the activity of α2PI of each of the specimen (n=2) having a concentration of 0 to 200% and α2PI specimen (n=10) having a concentration of 50% or 100% was measured using a plasmin solution of 10% glycyl glycine containing 10% glycerol, whereby the calibration curve exactness and its reproducibility were studied. Upon the study of the calibration curve exactness, the specimen was used in an amount of 10 μl because the stock solution of the normal plasma specimen was set to have an α2PI concentration of 200%. Upon the study of the reproducibility, the specimen was used in an amount of 5 μl because the stock solution of the normal plasma specimen was set to have an α2PI concentration of 100%. The results are shown in FIG. 1 and Table 5.

TABLE 5

| Concentration (%) | | | | | | | | | | | Average | SD | CV |
|---|---|---|---|---|---|---|---|---|---|---|---|---|---|
| 50% | 52 | 55 | 54 | 55 | 57 | 54 | 57 | 57 | 60 | 58 | 56 | 2.33 | 4.17 |
| 100% | 106 | 105 | 105 | 106 | 107 | 99 | 104 | 102 | 105 | 107 | 105 | 2.46 | 2.35 |

It has been found that from the results of FIG. 1, the plasmin solution had a good calibration curve property and from the results of Table 6, it has good reproducibility.

Industrial Applicability

The plasmin solution according to the present invention can be maintained stably without deteriorations in the plasmin activity and binding activity with α2PI even after long term storage and is therefore useful as a reagent for the quantitative measurement of α2PI. Moreover, it can be stored stably in the form of a solution so that it can be used as is at the time of measurement, which makes it possible to carry out measurement conveniently and promptly with excellent economy and operability. Furthermore, it has low viscosity so that it can be suitably used in the measurement by an automatic analyzer.

We claim:

1. A plasmin solution, comprising:
    (A) plasmin, and
    (B) the following component (B-1), (B-2) or (B-3):
    (B-1) an oligopeptide comprising at least two amino acids bonded to each other, said two amino acids being selected from the group consisting of lysine, arginine, glycine, alanine, aspartic acid and methionine;
    (B-2) at least two amino acids selected from the group consisting of lysine, arginine, glycine, alanine, aspartic acid and methionine; or
    (B-3) an amino acid selected from the group consisting of lysine, arginine, glycine, alanine, aspartic acid and methionine, and a polyhydric alcohol.

2. A plasmin solution according to claim 1, which comprises (B-1) or (B-2) as the component (B) and further comprises a polyhydric alcohol.

3. The plasmin solution according to claim 1, wherein the plasmin has an activity of 0.1 to 10 nkat/ml.

4. A plasmin solution according to claim 1, which comprises (B-1) as the component (B) and further comprises at least one amino acid selected from the group consisting of lysine, arginine, glycine, alanine, aspartic acid and methionine.

5. A plasmin solution according to claim 4, further comprising a polyhydric alcohol.

6. The plasmin solution according to claim 1, comprising (B-2).

7. The plasmin solution according to claim 6, wherein said at least two amino acids comprise lysine and glycine or lysine and alanine.

8. The plasmin solution according to claim 6, which comprises 1 to 20 wt. % of said at least two amino acids.

9. The plasmin solution according to claim 1, comprising (B-3).

10. The plasmin solution according to claim 9, wherein (B-3) is lysine.

11. The plasmin solution according to claim 9, which comprises 1 to 20 wt. % of (B-3).

12. The plasmin solution according to claim 1, comprising (B-1).

13. The plasmin solution according to claim 12, which comprises 1 to 20 wt. % of the oligopeptide.

14. The plasmin solution according to claim 12, wherein the oligopeptide is a dipeptide or a tripeptide.

15. The plasmin solution according to claim 14, wherein the oligopeptide is selected from the group consisting of glycyl glycine, glycyl glycyl glycine and alanyl alanine.

16. A method of binding plamsin to α2PI, comprising contacting said α2PI with an amount of the plasmin solution according to claim 1 effective to bind the plasmin to said α2PI.

17. A process for stabilizing plasmin, which comprises adding, to a plasmin solution, as an additive:

(B-1) an oligopeptide comprising at least two amino acids bonded to each other, said two amino acids being selected from the group consisting of lysine, arginine, glycine, alanine, aspartic acid and methionine;

(B-2) at least two amino acids selected from the group consisting of lysine, arginine, glycine, alanine, aspartic acid and methionine; or (B-3) an amino acid selected from the group consisting of lysine, arginine, glycine, alanine, aspartic acid and methionine, and a polyhydric alcohol.

18. A process according to claim 17, which comprises adding (B-1) or (B-2) as the additive and further comprising adding a polyhydric alcohol.

19. A process according to claim 17, which comprises adding (B-1) as the additive and further comprises adding at least one amino acid selected from the group consisting of lysine, arginine, glycine, alanine, aspartic acid and methionine.

20. A process according to claim 19, which further comprises adding a polyhydric alcohol.

* * * * *